(12) United States Patent
Hommann et al.

(10) Patent No.: US 7,125,395 B2
(45) Date of Patent: Oct. 24, 2006

(54) DEVICE FOR CONTROLLED DELIVERY OF AN INJECTABLE LIQUID

(75) Inventors: Edgar Hommann, Grossaffoltern (CH); Christof Kuenzi, Bolligen (CH)

(73) Assignee: TecPharma Licensing AG, Burgdorf (CH)

(*) Notice: Subject to any disclaimer, the term of this patent is extended or adjusted under 35 U.S.C. 154(b) by 88 days.

(21) Appl. No.: 10/650,521

(22) Filed: Aug. 28, 2003

(65) Prior Publication Data
US 2004/0054326 A1    Mar. 18, 2004

(30) Foreign Application Priority Data
Aug. 30, 2002    (DE) ................ 102 40 166

(51) Int. Cl.
*A61M 5/20* (2006.01)
*A61M 5/00* (2006.01)
*A61M 5/315* (2006.01)

(52) U.S. Cl. ............. 604/135; 604/211; 604/223; 604/228

(58) Field of Classification Search ........ 604/131, 604/134, 135, 154, 155, 187, 207, 208–209, 604/210–211, 218, 220, 223–224, 225, 228, 604/246
See application file for complete search history.

(56) References Cited

U.S. PATENT DOCUMENTS 4,300,554 A * 11/1981 Hessberg et al. .......... 604/135
4,568,335 A * 2/1986 Updike et al. ............. 604/211
5,112,311 A * 5/1992 Utterberg et al. .......... 607/177
5,261,882 A * 11/1993 Sealfon .................... 604/135
6,482,186 B1 * 11/2002 Douglas et al. ........... 604/128

FOREIGN PATENT DOCUMENTS

| DE | 33 31 424 A1 | 3/1984 |
|----|--------------|--------|
| DE | 43 04 544 A1 | 8/1994 |
| WO | WO 95/09021 | 4/1995 |
| WO | WO 98/57688 | 12/1998 |
| WO | WO 01/19434 A1 | 3/2001 |
| WO | WO 01/78812 A1 | 10/2001 |
| WO | WO 01/83008 A1 | 11/2001 |
| WO | WO 01/87386 A1 | 11/2001 |
| WO | WO 02/28455 A1 | 4/2002 |

* cited by examiner

Primary Examiner—Catherine S. Williams
(74) Attorney, Agent, or Firm—Dorsey & Whitney LLP (57) ABSTRACT

A device for the controlled delivery of an injectable liquid from a liquid container, wherein a flexible force transferring means transfers the drive force of a drive wheel onto a piston which can be slid axially in the device, a preferably permanently acting restoring force of a spiral spring is applied to the drive wheel in order to advance the piston and expel the liquid, and a locking means locks the drive wheel against rotation and releases the drive wheel to expel the liquid. In one embodiment, the amount of liquid expelled can be indicated by audible clicks and, in one embodiment, the drive wheel moves only incrementally when the locking mechanism releases the drive wheel.

23 Claims, 6 Drawing Sheets

DEVICE FOR CONTROLLED DELIVERY OF AN INJECTABLE LIQUID

CROSS-REFERENCE TO RELATED APPLICATION

This application claims priority to German Application No. 102 40 166.7, filed on Aug. 30, 2002.

BACKGROUND

The present invention relates to a device for the controlled delivery of an injectable liquid, in one embodiment, from a preferably substantially cylindrical liquid container. More particularly, the present invention relates to an injection device for administering a liquid containing a therapeutic or medical active agent, for example insulin for the treatment of diabetes, from a syringe body.

Injection devices of the aforementioned type are known for example from WO 95/09021. A syringe body for storing the liquid to be administered is sealed off at a rear end by a piston which can be slid axially in the syringe body, the liquid being delivered from an outlet at the front end of the syringe body when the piston is advanced towards the outlet. While in conventional injection devices comprising syringe bodies, the overall length must correspond to at least twice the maximum stroke of the piston which can be slid in the syringe body, the overall length can be reduced in injection devices of the aforementioned type by axially deviating a piston rod behind the syringe body, which drives the piston, away from its longitudinal axis. This is in particular advantageous in portable injection devices for autotherapy.

WO 95/09021 discloses a substantially incompressible, flexible piston rod which is tightly guided in a guide in order to prevent the piston rod from bending laterally away from its longitudinal axis. The piston is advanced by controlled rotation of a threaded rod, the rotational movement being converted into an advancing movement by means of a rotationally fixed but longitudinally slidable nut which engages with the outer thread of the threaded rod and is connected to the rear end of the flexible piston rod. This mechanism is hardly suitable for hand-operated injection devices without an energy supply of their own. In addition, the drive mechanism is comparatively elaborate.

An injection device operating according to the aforementioned basic principle is disclosed in WO 98/57688. When an operating button is depressed, a downward movement of a first gear rack is converted into an upward movement of a second gear rack which is coupled to a flexible piston rod. By rotating a dosage setting wheel, a stopper is adjusted within an adjustment range defined by maximum end positions, in order to set the dosage to be administered. The second gear rack can be maximally slid only by the distance pre-set by the stopper. Furthermore, a first spring is provided to reset the operating button, and a second spring which is provided in a dosage setting mechanism. The two springs are not coupled to the drive mechanism, in order to reset the latter and advance the piston for delivering liquid from the syringe body. Although the mechanism disclosed in WO 98/57688 can be operated by hand, it has a comparatively elaborate design.

SUMMARY

It is an object of the present invention to provide a generic device comprising a simpler mechanism which is hand-operable.

This object is addressed by a device for the controlled delivery of an injectable liquid from a liquid container which is sealed off at a rear end by a piston which can be slid axially in said container in order to deliver the liquid from an outlet at a front end of the container, the device comprising, in one embodiment, a flexible force transferring means which is axially deviated, behind the container, away from the longitudinal axis of the container; a drive mechanism which is coupled to said flexible force transferring means, in order to axially advance the piston for delivering the liquid; and a restoring means, wherein said restoring means applies a restoring force to said drive mechanism and resets it for delivering liquid from the container, in order to advance the piston via the flexible force transferring means.

In one embodiment, the present invention comprises a device for the controlled delivery of an injectable liquid from a liquid container wherein: a flexible force transferring means transfers a drive force of a rotatable drive wheel onto a piston which can be slid axially in the device, a restoring force of a spring is applied to the drive wheel to move the piston, and a locking means locks the drive wheel against rotation and releases the drive wheel for rotation. In one embodiment, the amount of liquid expelled may be indicated by audible clicks and, in one embodiment, the drive wheel moves incrementally when the locking means releases the drive wheel.

In one embodiment, the present invention comprises a device for the controlled delivery of an injectable liquid from a liquid container wherein: a flexible force transferring means transfers the drive force of a drive wheel onto a piston which can be slid axially in the device, a preferably permanently acting restoring force of a spiral spring is applied to the drive wheel in order to advance the piston and expel the liquid, and a locking means locks the drive wheel against rotation and releases the drive wheel to expel the liquid. In one embodiment, the amount of liquid expelled can be indicated by audible clicks and, in one embodiment, the drive wheel moves only incrementally when the locking mechanism releases the drive wheel.

In accordance with the invention, the drive mechanism serving to advance the piston is coupled to a restoring means which resets it for delivering liquid from the container, in order to advance the piston via the flexible force transferring means. The restoring means is characterized by a restoring force which applies a restoring force to the drive mechanism. Thus, in accordance with the invention, a separate drive motor for advancing the piston is not required, nor is a complicated mechanism, for example a gear mechanism, to convert a drive force of the drive motor into an advancement of the piston.

For delivering liquid, it is only necessary in accordance with the invention to release the restoring force of the restoring means, which can be achieved by a simple release mechanism.

In one embodiment, the restoring force is preferably characterized by a preferential direction in which it resets the drive mechanism into an end position in which the restoring force is negligible and the drive mechanism no longer continues driving. The end position of the restoring means preferably corresponds to a front end position of the piston, where the piston is situated substantially at the front end of the liquid container.

In the direction opposite to the aforementioned preferential direction, by contrast, the drive mechanism is not driven by the restoring means. This ensures that, once the restoring force has been released, the piston is driven towards the outlet of the liquid container.

Another advantage is that restoring means can be realized simply, for example by means of pressure or tension springs or coil springs for generating a rotational restoring force. In principle, the restoring force can also be generated in other ways, for example electrically, magnetically or pneumatically.

In some preferred embodiments, the restoring force is permanently applied to the drive mechanism, in which case only a simple release mechanism is provided to release the restoring force for advancing the piston in the liquid container.

In some preferred embodiments, an adjustable, mechanical locking means is provided, for a controlled release of the restoring force and to lock against angular adjustment of the drive wheel, except when the locking means releases the rotational movement of the drive wheel. Mechanical locking means can advantageously be realized in a simple way by means of blocking pins, teeth or comparable latching protrusion and latching recesses. The present invention is not, however, in principle restricted to mechanical locking means. Rather, the restoring force can also be released and/or blocked by electrical, magnetic or pneumatic means.

One simple embodiment results if the locking means is configured as a simple rocking lever which is moved to a releasing position, in which the drive mechanism is released, by advancing an operating button, and can be reset into a locking position, in which the drive mechanism is locked, by a second restoring means. The rocking lever, or elements cooperating with it, comprises a mechanical blocking means, for example a blocking projection, which cooperates with a corresponding mechanical blocking means, for example a teeth on a lateral facing area of the drive wheel.

BRIEF DESCRIPTION OF THE DRAWINGS

Embodiments of the present invention, including preferred embodiments, will now be described by way of example and by referring to the accompanying drawings.

In the figures, identical reference numerals indicate substantially identical or substantially functionally identical elements and sub-assemblies.

DETAILED DESCRIPTION

Figure 1:
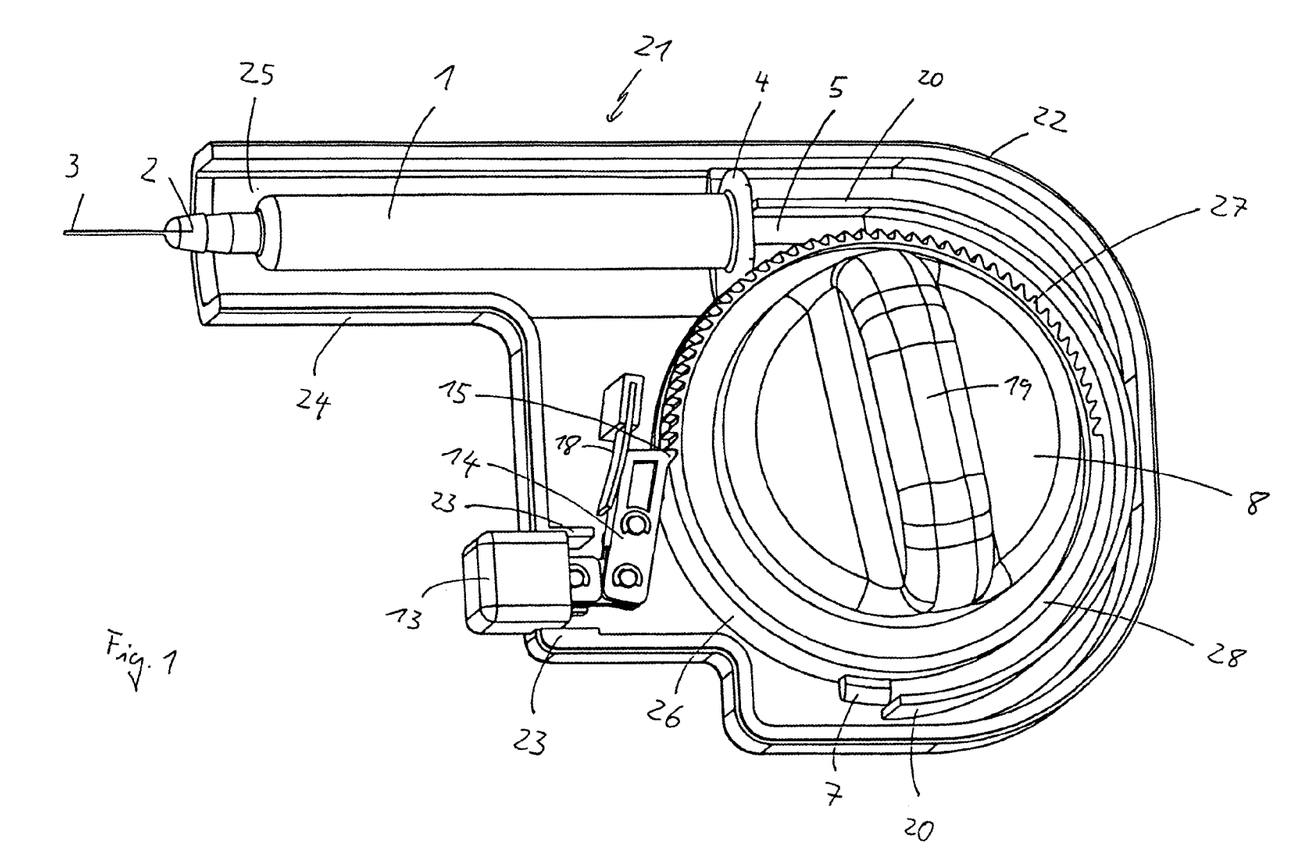
FIG. 1 depicts an injection device in accordance with one embodiment of the present invention, with the upper half-casing removed, in a perspective top view.
Figure 2:
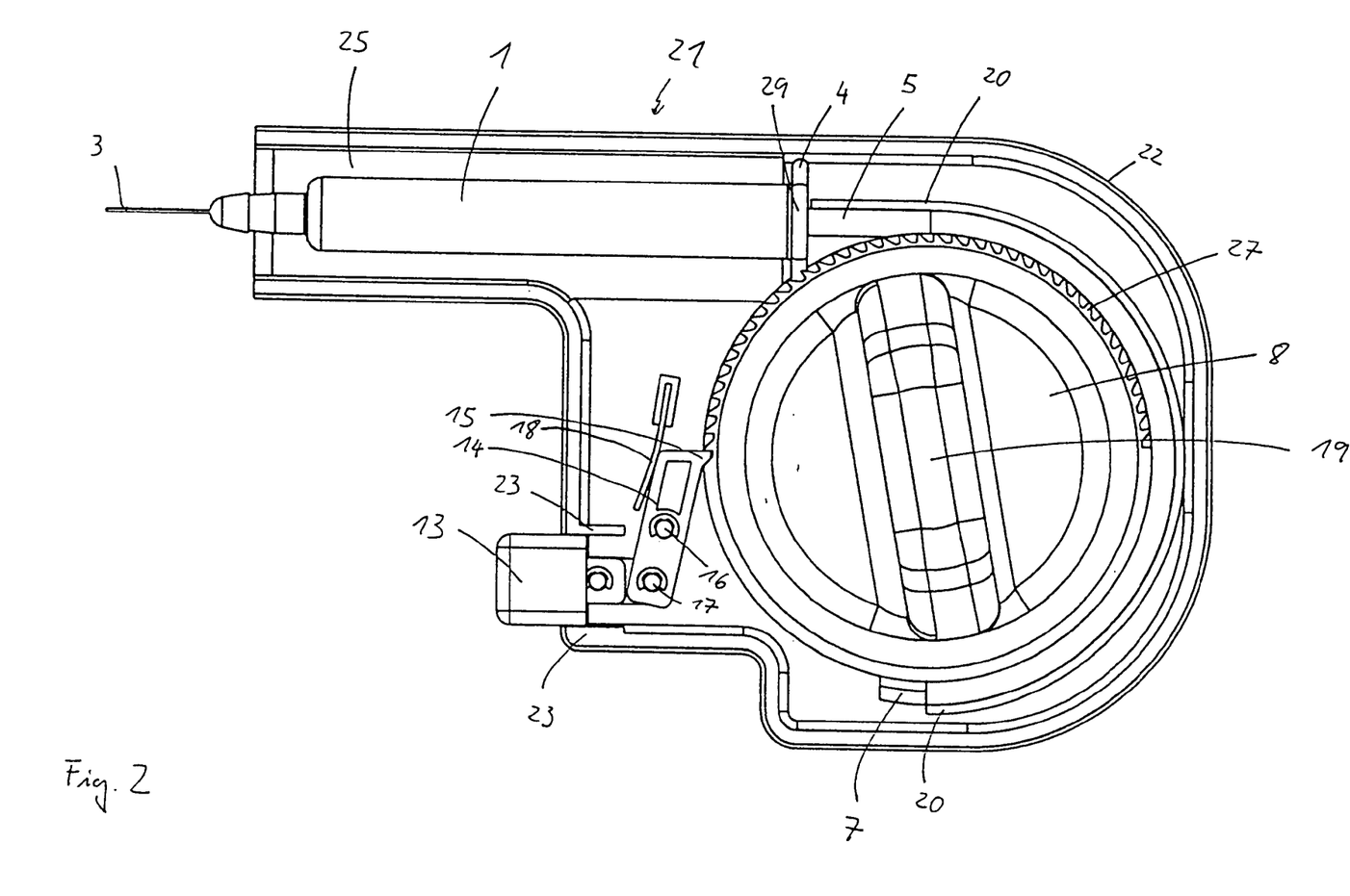
FIG. 2 depicts the device in accordance with FIG. 1, with the upper half-casing removed, in a top view.

FIG. 1 shows a perspective top view of one embodiment of an injection device in accordance with the invention, with the upper half-casing removed. The injection device comprises a substantially cylindrical syringe body 1 which serves to store the liquid to be administered, which preferably contains a therapeutic or medical active agent, for example insulin for treating diabetes. The syringe body 1 is sealed off at its rear end 4 by a piston (not shown) and comprises an injection needle 3 including a needle support 2 at its front end, said needle support being connected to the syringe body 1. The piston can be slid axially in the syringe body and delivers liquid from the injection needle 3 when it is advanced towards the front end 2.

In one embodiment, a flexible force transferring means 5 is provided for advancing the piston, wherein the front end of said force transferring means 5 abuts the piston (not shown) or is connected to it, preferably detachably. The force transferring means 5 is preferably incompressible and consists of a plastic or metal or comparable materials. As shown in FIG. 1, the force transferring means 5 is axially deviated, behind the syringe body 1, away from the longitudinal axis of the syringe body 1, such that the overall length of the injection device shown can be reduced as compared to conventional injection devices. In the region 7, the force transferring means 5 is coupled, preferably fastened, to the drive wheel 8 which serves as the drive mechanism, and serves to transfer the drive force generated by the drive mechanism 8 onto the piston (not shown), in order to advance the latter into the syringe body 1.

The drive wheel 8 is substantially circular and comprises an outer toothed area 27 in a first half on a lateral facing side and the fastening region 7, for coupling the force transferring means 5 to the drive wheel 8, in a second half opposite the outer area 27. The drive wheel 8 comprises a handle 19 on its upper side, wherein said handle protrudes through the upper half-casing (not shown) of the injection device and can be operated from the outer side of the casing. The grip 19 serves to rotate the drive wheel 8, in particular to reset the drive wheel 8 against the restoring force of the spiral spring 10 shown in FIGS. 3 and 4, which serves as the restoring means.

Radially inwardly, the flexible force transferring means 5 either directly abuts the outer circumference of the drive wheel 8 or abuts a stay corresponding to the outer contour of the drive wheel 8, said stay protruding substantially perpendicularly from the lower half-casing 21. Radially outwardly, the flexible force transferring means 5 abuts the stay 20 projecting substantially perpendicularly from the lower half-casing 21. Furthermore, a guiding area is provided in the lower half-casing 21 in the region between the outer circumference of the drive wheel 8 or the radially inner stay (not shown) and the radially outer stay 20, as well as correspondingly in the upper half-casing (not shown), the flexible force transferring means 5 substantially abutting said guiding area. Together, the stays and the guiding areas form a guide which tightly abuts the force transferring means, said guide preventing or at least as far as possible inhibiting the force transferring means from bending laterally, away from its longitudinal axis.

Figure 3:
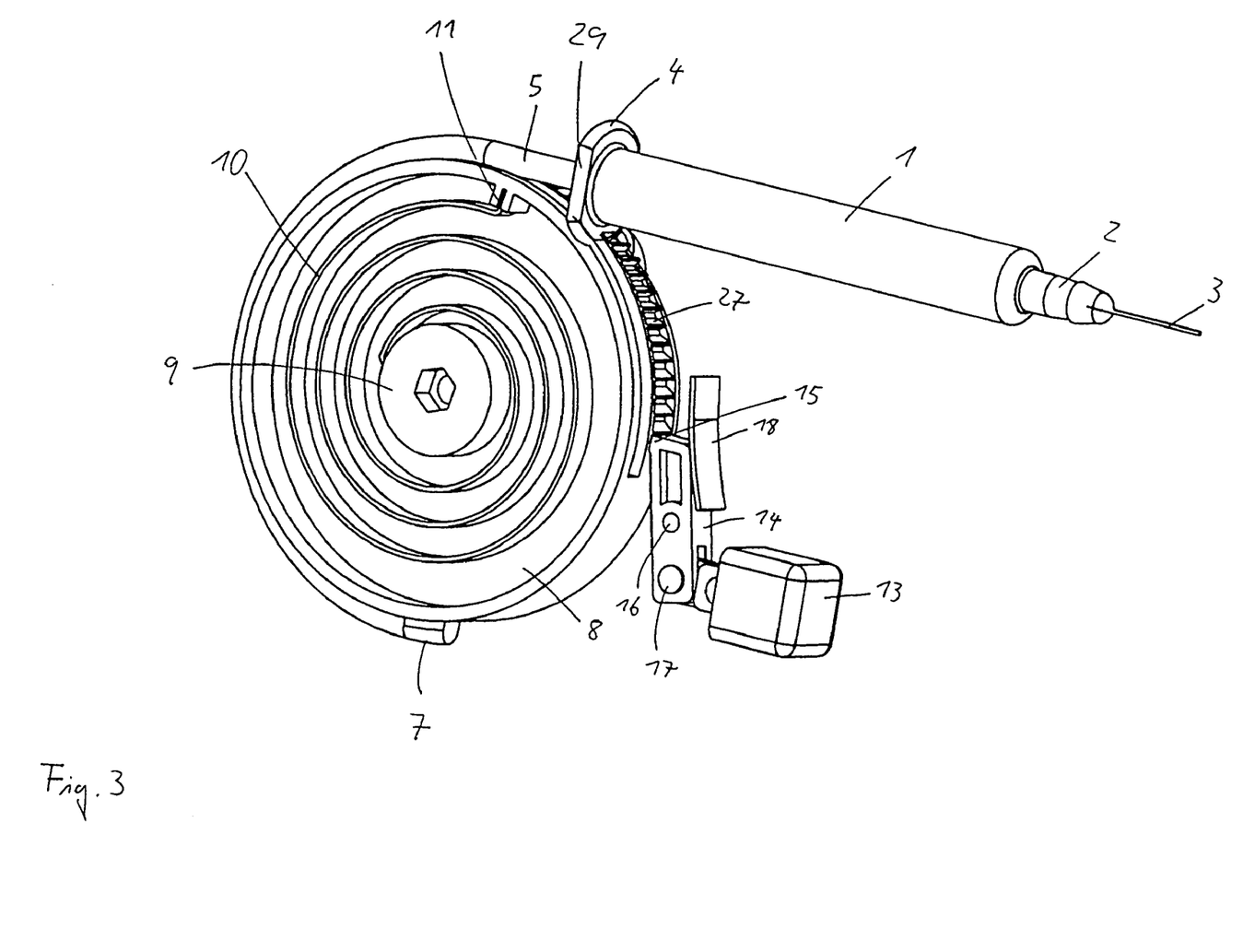
FIG. 3 depicts the device in accordance with FIG. 1, from the rear side, without the outer half-casings, in a perspective view.
Figure 4:
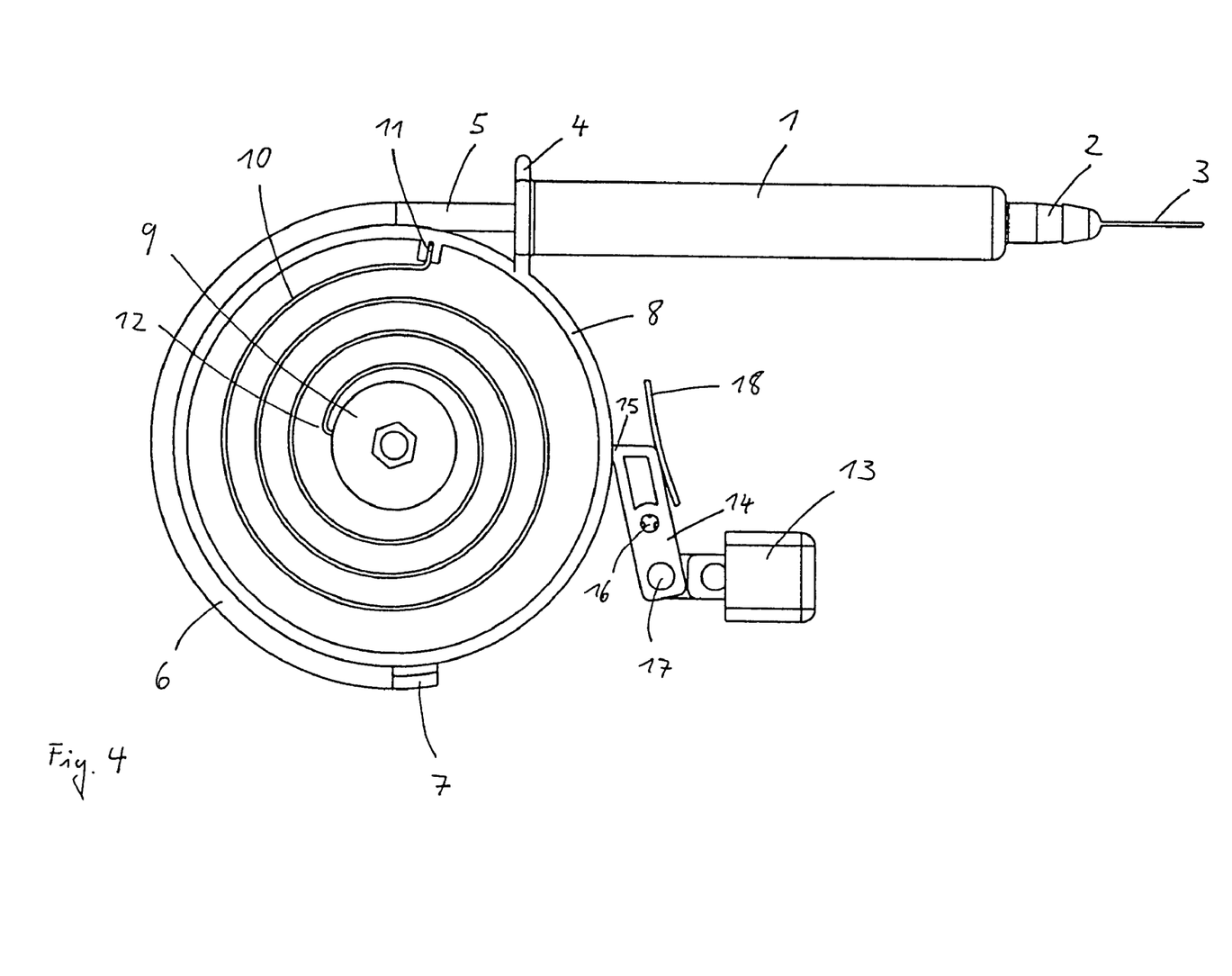
FIG. 4 depicts the device in accordance with FIG. 1, from the rear side, without the outer half-casings, in a top view.

FIGS. 3 and 4, which show the first embodiment from the rear side in a perspective top view (FIG. 3) and a schematic top view (FIG. 4) with the lower half-casing 21 removed, show how a spiral spring 10 serving as the restoring means is connected to the drive wheel 8. At the radially outer end of the spiral spring 10, one end of the spring, bent away at a right angle, is hung in a first fastening point 11, while at the radially inner end of the spring 10, a section of the spring, bent away substantially at a right angle, is hung in a radially inner fastening point 12. One of the two fastening points 11, 12 is connected to the lower half-casing (not shown), while the other of the fastening points 11, 12 is connected to the drive wheel 8. Thus, the spring 10 biases the drive wheel 8 against the half-casings of the injection device. The bias force can be achieved by reversing the handle 19 (FIG. 1) or using motors. In some embodiments, the bias force is preferably of such a magnitude that the piston can be advanced between its rear end position, i.e., substantially the rear end 4 of the syringe body 1, and its front end position, i.e., substantially the front end 2 of the syringe body 1, due to the restoring force of the spring 10.

Another suitable restoring means can be used instead of the spiral spring shown in FIGS. 3 and 4. The restoring means does not necessarily need to be directly connected to the drive wheel 8, but can also, for example, act on its rotational mount in order to reverse it in the advancing direction of the piston.

The spiral spring 10 shown in FIGS. 3 and 4 permanently applies the restoring force to the drive wheel 8. The present invention is not, however, restricted to a permanently acting restoring force. For locking against angular adjustment of the drive wheel 8, a locking means is provided, in particular in embodiments with a permanently acting restoring force. In accordance with FIGS. 1 to 4, the locking means is formed by a rocking lever 14 which supports a blocking projection 15 at its front end, wherein said blocking projection 15 is formed to correspond to the outer teeth or toothed area 27 and cooperates with the same, such that the drive wheel 8 is prevented from being turned further due to the permanently acting restoring force.

The rocking lever 14 pivots about the rotational point 16 (FIG. 2) between the locking position shown in FIGS. 1 to 4, in which the engagement between the blocking projection 15 and the outer toothed area 27 locks against angular adjustment of the drive wheel 8, and a releasing position in which the blocking projection 15 releases the engagement with the outer area 27 such that the drive wheel 8 is rotated in the advancing direction of the piston, i.e. in FIG. 1, anti-clockwise, due to the restoring force of the spring 10.

The rocking lever 14 is connected via the joint 17 to the operating button 13 which is linearly guided in lateral stays 23 of the lower half-casing 21 and can be pushed into the casing of the injection device. At the other end of the rocking lever 14, on the side of the rotational point 16 opposite the joint 17, a leaf spring 18 serving as a second restoring means acts on the rocking lever 14 in order to reverse it into the locking position.

In the injection device shown, in one embodiment, the maximum piston stroke of the piston between the rear end 4 and the front end 2 of the syringe body 1 corresponds to an angular adjustment of the drive wheel 8, defined substantially by the radius of the guide 20 for the flexible force transferring means 5. Stoppers (not shown) are preferably provided in the casing and/or on the drive wheel 8 and/or on the flexible force transferring means 5, and limit the angular adjustment of the drive wheel 8 in its two end positions. Preferably, the maximum piston stroke of the piston in the syringe body 1 corresponds to the bending radius of the flexible force transferring means 5 multiplied by the number pi. The piston is thus slid between its rear and front end position by half a revolution of the drive wheel 8. Thus, in the embodiment shown in FIGS. 1 to 4, the outer toothed area 27 can be arranged in a first half of the drive wheel 8, while the fastening region 7, in the rear end position of the piston in the syringe body 1, is substantially arranged diametrically opposite the rear end 4 of the syringe body 1. The present invention is not, however, restricted to the aforementioned dimensions.

In order to even more flexibly exchange the syringe body 1, the front end 24 of the lower half-casing 21 and/or the corresponding front end of the upper half-casing (not shown) can be removable, in order to make the syringe body 1 fully accessible for exchanging. In some preferred embodiments, the front end 24 comprises a bearing area 25 on its inner side, said bearing area 25 being formed to correspond exactly to the outer contour of the syringe body 1, in order to securely store it. In order to insert the syringe body 1 into the bearing area 25 of the front end 24 of the injection device in an exact fit, the rear end 4 of the syringe body 1 comprises the flattened portion 29 visible in FIGS. 2, 3 and 5. The piston of the syringe body 1 can be retracted by reversing the drive wheel 8 against the restoring force of the spring 10. The syringe body 1 can then be removed from the casing.

In one embodiment the injection device may be operated as follows: the flexible force transferring means 5 is retracted by reversing the drive wheel 8, clockwise in FIG. 1. At the same time, the piston (not shown) can also be moved to its rear end position near the rear end 4 of the syringe body 1. Once the front half-casing 24 has been removed, the syringe body 1 can be replaced with a new syringe body. The flexible force transferring means 5 is then moved back to abut the piston or is connected to it. The piston is then sufficiently advanced, for example to prime the syringe body. In the rear end position which the piston then reaches, the blocking projection 15 engages with the outer toothed area 27 of the drive wheel 8 and locks against its angular adjustment. In this position, the front end of the operating button 13 protrudes out of the lower half-casing 21.

Pushing the operating button 13 into the casing releases the blocking projection 15 from the outer toothed area 27, such that there is a controlled release of the restoring force by the locking means. Lastly, the engagement between the blocking projection 15 and the outer toothed area 27 is completely or substantially completely released. Due to the restoring force of the spring 10, the drive wheel 8 then turns, anti-clockwise in FIG. 1, and thereby slaves the flexible force transferring means 5 connected to the drive wheel 8 in the region 7. The front end of the flexible and incompressible force transferring means 5, guided in the guide 20, is thus axially advanced in the syringe body 1 and thereby slaves the piston stopper, such that liquid is delivered from the injection needle 3.

As long as the operating button 13 is sufficiently pushed down, in order to release the drive wheel 8, the piston is advanced into the syringe body 1 due to the restoring force, and liquid is expelled. While the drive wheel 8 rotates, clearly audible clicks can be generated for the user, for example because the teeth in the outer toothed area 27, or dosing protrusions attached at regular angular intervals to the facing sides or lateral areas of the drive wheel 8, abut an obstacle and thereby emit the click. In principle, the blocking projection 15 shown in the figures is also suitable as an obstacle, providing the distance between the blocking projection 15 and the teeth of the outer toothed area 27 is sufficiently small in the releasing position of the rocking lever 14 that on the one hand the blocking projection 15 and the outer toothed area 27 abut, but on the other this does not prevent the drive wheel 8 from turning further.

The restoring force of the spring 10 serving as the restoring means can be adjusted to the flow resistance of the liquid as it is delivered from the syringe body 1, such that there remains enough time for the user to count out the clicks and so work out the dosage of liquid actually delivered.

The user then lets go of the operating button 13 again. Due to the restoring force of the leaf spring 18 serving as the second restoring means, and/or a spring (not shown) which pushes the operating button 13 back out of the casing, the rocking lever 14 is reset into the locking position. Because the steep flanks of the serrated-toothed outer toothed area 27 each lie on the side of the tooth flanks of the outer toothed area 27 lying in the restoring direction, the correspondingly formed blocking projection 15 is automatically returned to the locking position as soon as a front end of the blocking projection 15 comes to abut one of the tooth flanks of the outer toothed area 27. The expulsion of liquid is thus automatically terminated when the user lets go of the operating button 13.

In principle, however, it can also be provided that the restoring force of the leaf spring 18 and/or the spring (not shown) which pushes the operating button 13 back out of the casing are too small to move the blocking projection 15 back into engagement with the toothed area 27, when the drive wheel 8 is turning. In such an embodiment, the entire dosage of liquid still available in the syringe body 1 would then be completely administered.

Figure 5:
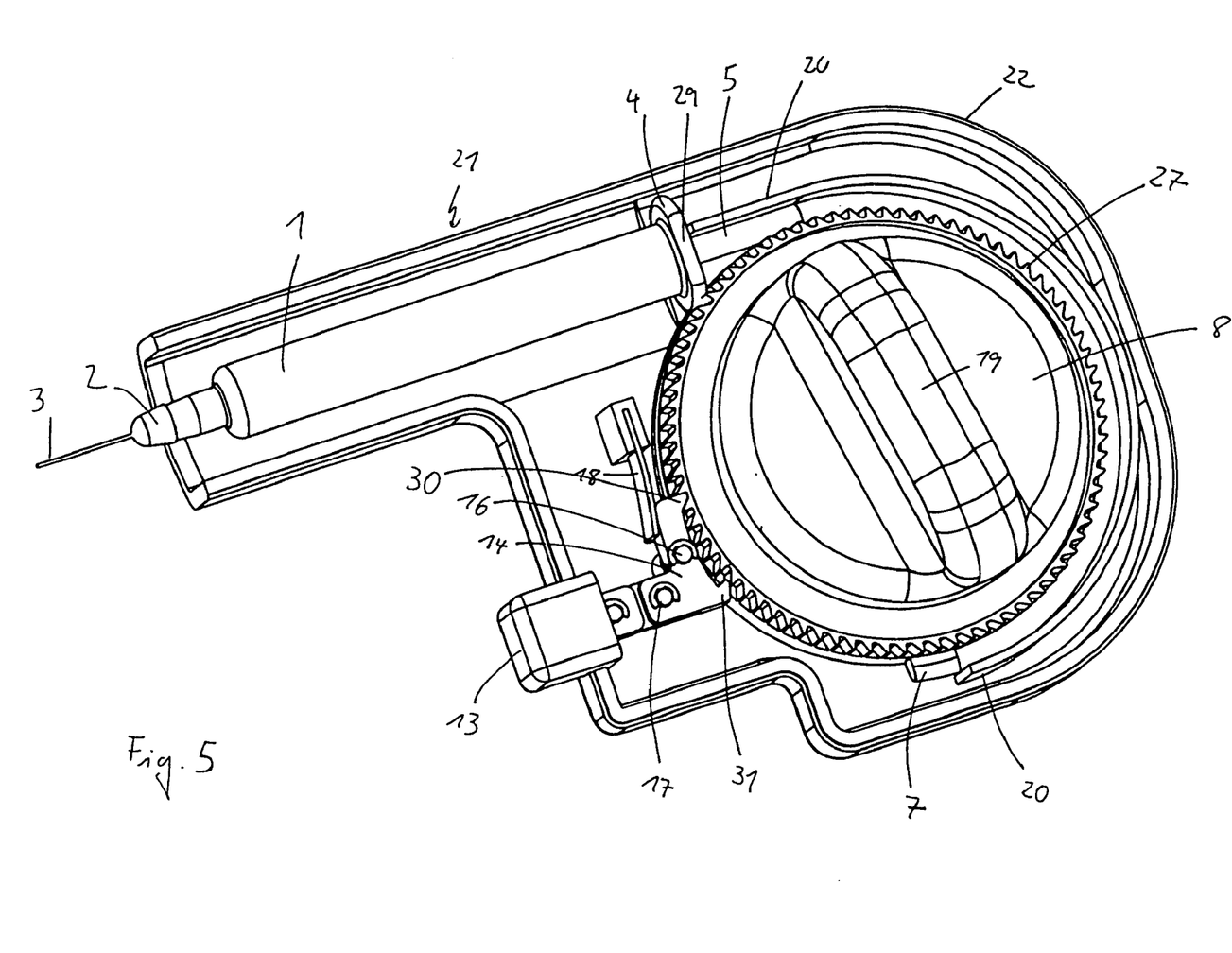
FIG. 5 depicts an injection device in accordance with another embodiment of the present invention, with the upper half-casing removed, in a perspective top view.
Figure 6:
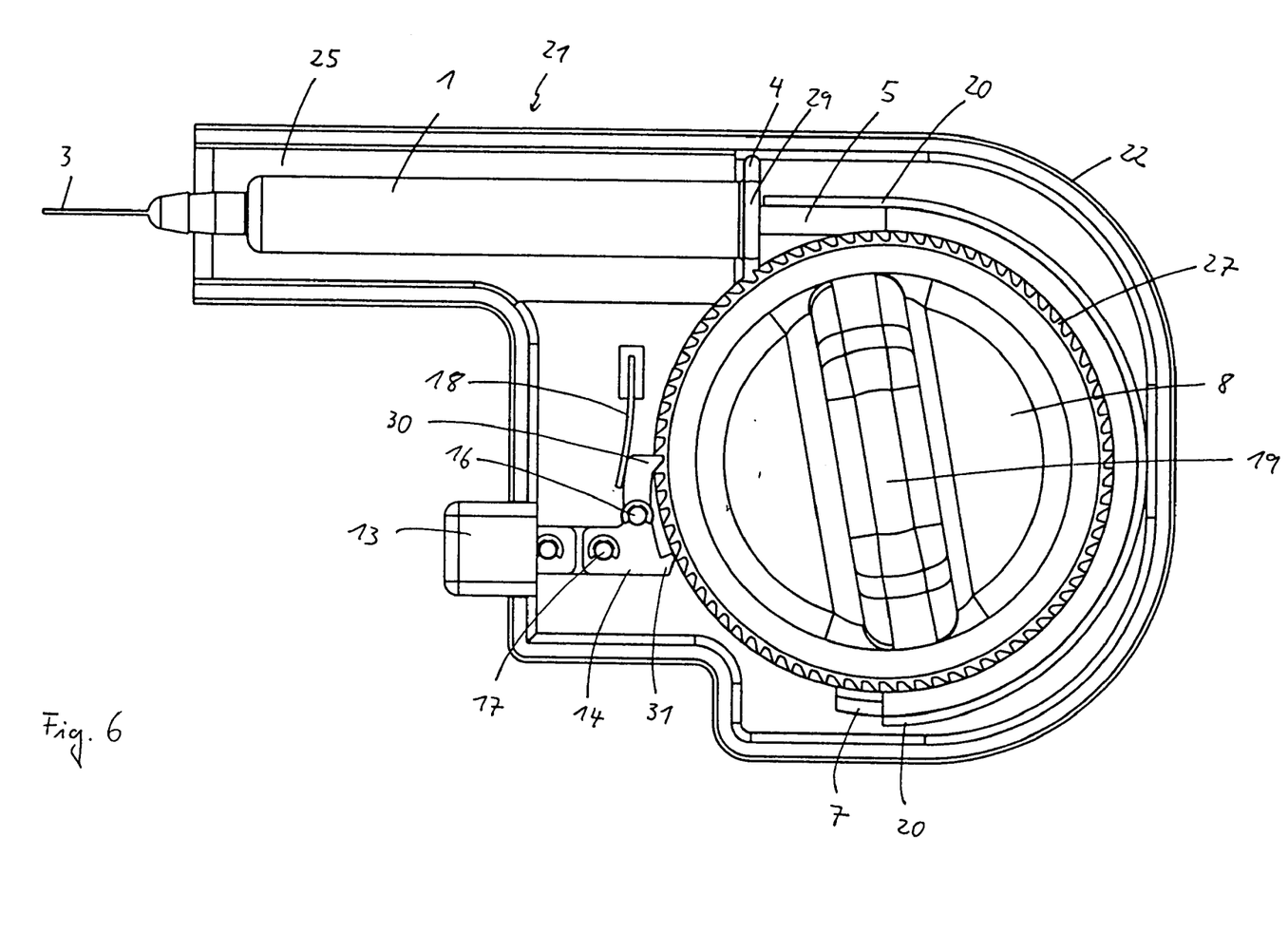
FIG. 6 depicts the device in accordance with FIG. 5, with the upper half-casing removed, in a schematic top view.

In order to even more simply dose the amount of liquid actually delivered using the injection device in accordance with the invention, the locking means is configured, in another embodiment shown in FIGS. 5 and 6, such that the piston can only be moved a fraction of the maximum piston stroke pre-set by the front and rear end positions of the piston in the syringe body 1. In principle, identical reference numerals in FIGS. 5 and 6 indicate identical components and functional groups, such that a description of them is omitted below for reasons of clarity.

FIGS. 5 and 6 show a second embodiment of the injection device in accordance with the invention from above, with the upper half-casing removed, in a perspective top view and a schematic top view. In accordance with the second embodiment, the rocking lever 14 as a whole is formed substantially L-shaped. The upper limb of the rocking lever 14 is jointed via a joint 17 coupled to the operating button 13. The lower limb of the rocking lever 14 comprises two blocking projections 30, 31 arranged on opposite sides of the rotational point 16 of the rocking lever 14, which are each formed to correspond to the teeth of the outer toothed area 27 of the drive wheel 8, but which, as can be seen in FIG. 6, are offset with respect to each other by half a tooth of the outer toothed area 27. Thus, if one of the blocking projections 30, 31 engages completely with the outer toothed area 27, then the other of the blocking projections 30, 31 is arranged approximately in the middle of a tooth flank of the outer toothed area 27.

In the resting position of the operating button 13, shown in FIGS. 5 and 6, the first blocking projection 30 engages with the outer toothed area 27 and locks against angular adjustment of the drive wheel 8. If the operating button 13 is then pushed down into the casing, the rocking lever 14 is pivoted about the rotational point 16 such that the first blocking projection 30 is released from its engagement with the outer toothed area 27 and the second blocking projection 31 is moved to the middle of the opposite tooth flank of the outer toothed area 27. Lastly, the second blocking projection 31 comes to abut the opposite tooth flank. If the operating button 13 is pushed further down, the second blocking projection 31 slides off, ultimately completely, on the opposite tooth flank and engages, ultimately completely, with the outer toothed area 27. In this position, the first blocking projection 30 is preferably completely out of engagement with the outer toothed area 27 and the drive wheel 8 has turned further by half a tooth flank, anti-clockwise in FIG. 6. This rotational movement of the drive wheel 8 is assisted by the restoring force, acting in the same direction, of the spiral spring 10 serving as the restoring means (see FIGS. 3, 4).

The user then lets go of the operating button 13 again. Due to the restoring force of the leaf spring 18, serving as the second restoring means and abutting the rocking lever 14 in the region of the first blocking projection 30, and of a spring (not shown) which pushes the operating button 13 back out of the casing of the injection device, the second blocking projection 31 is gradually released from its engagement with the outer toothed area 27 and the first blocking projection 30 is moved back into engagement with the outer toothed area 27. Here, too, the first blocking projection 30 slides off, ultimately completely, on the tooth flank opposite it until the first blocking projection 30 engages, ultimately completely, with the outer toothed area 27 and locks against further angular adjustment of the drive wheel 8.

In accordance with the second embodiment, when the operating button 13 is operated once, the drive wheel 8 is turned further by exactly one tooth flank of the outer toothed area 27. This corresponds to a minimum amount of liquid which can be dosed by the injection device. Operating the operating button 13 is easily tangible. The user can thus easily set the dosage of liquid actually delivered by simply counting the number of times, however often, the operating button 13 is operated. When rotating the drive wheel 8, clicks can again be generated, as described above, such that the user can also select or calculate the dosage of liquid by sound.

In the above embodiments, the flexible force transferring means 5 is preferably a cylindrical coil spring made of round wires having a constant diameter. The cylindrical cross-section of coil springs enables them to be guided easily, for example using the stays 20 shown in the figures, which project substantially perpendicularly from the lower or upper half-casing, or using comparable guiding means. In addition, metallic coil springs slide on the guiding stays described above, preferably formed from plastic, with comparatively little resistance.

In principle, however, the flexible force transferring means can also be made from plastic, for example in the form of an articulated plastic band such as is disclosed in WO 98/01173, the content of which is expressly incorporated herein by way of reference.

In the above embodiments, the drive wheel 8 can also be latched in ways other than using the outer toothed area 27 and the blocking projection 15 which cooperates with it. Suitable teeth, texture or latching protrusions can, for example, be provided on an upper side of the drive wheel 8 or on a disc or the like coupled to a drive axle of the drive wheel 8, in order to cooperate with latching protrusions or the like of a locking means. Suitable measures will become clear to the person skilled in the art when studying this application.

While it has been described above that the operating button 13 is operated by hand by the user, a release mechanism operated using motors or electromagnetically can of course also be provided to trigger delivery of the liquid.

A preferred application of the injection device in accordance with the invention is the injection of insulin into subcutaneous fatty tissue, for treating diabetes. The invention is not, however, restricted to this application.

In the foregoing description, embodiments of the present invention, including preferred embodiments, have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A device for the controlled delivery of an injectable liquid from a liquid container sealed at a rear end by a piston which can be slid axially in said container to deliver the liquid from an outlet at a front end of the container, comprising:
 a drive mechanism;
 a flexible force transferring means axially deviated behind the container away from a generally central longitudinal axis of the container wherein the flexible force transferring means comprises a cylindrical coil spring coupled to a lateral facing area of the drive mechanism; and
 a restoring means rotatably mounted inside said drive mechanism, wherein said restoring means applies a restoring force to said drive mechanism such that said drive mechanism axially advances the piston for delivering liquid from the container.

2. The device as set forth in claim 1, wherein, absent a counter force, the restoring means permanently applies said restoring force to the drive mechanism in order to actuate it from a starting position in which the piston is situated substantially at the rear end of the liquid container to an end position in which the piston is situated substantially at the front end of the liquid container.

3. The device as set forth in claim 2, wherein, in the starting position of the piston, a region in which the flexible force transferring means is attached to the drive mechanism is substantially arranged diametrically opposite the rear end of the liquid container.

4. The device as set forth in claim 1, wherein the drive mechanism comprises a drive wheel and the flexible force transferring means is attached to a lateral facing area of said drive wheel.

5. The device as set forth in claim 4, further comprising an adjustable locking means for providing controlled locking against an angular adjustment of the drive wheel.

6. The device as set forth in claim 5, wherein said locking means comprises a blocking projection which cooperates with an outer toothed area of the drive mechanism.

7. The device as set forth in claim 1, wherein the drive mechanism is configured, when delivering the liquid, to emit a number of clicks corresponding to the dosage of liquid delivered.

8. The device as set forth in claim 1, wherein one of a 30-gauge or 31-gauge injection needle for injecting the liquid is provided on the front end of the container.

9. The device as set forth in claim 1, wherein said restoring means is adjacently coupled to said drive mechanism.

10. The device as set forth in claim 1, wherein said restoring means is a spiral spring with a radially outer end, said radially outer end being coupled to an inner surface of said drive mechanism.

11. A device for the controlled delivery of an injectable liquid from a liquid container sealed at a rear end by a piston which can be slid axially in said container to deliver the liquid from an outlet at a front end of the container, comprising:
 a flexible force transferrer axially deviated behind the container away from a generally central longitudinal axis of the container;
 a drive mechanism, wherein said flexible force transferrer is coupled to a lateral facing area of said drive mechanism;
 a restoring means rotatably mounted inside said drive mechanism, wherein said restoring means applies a restoring force to said drive mechanism such that said drive mechanism axially advances the piston for delivering liquid from the container; and
 an adjustable locking means for providing controlled locking against an angular adjustment of the drive mechanism wherein said locking means comprises a blocking projection which cooperates with an outer toothed area of the drive mechanism,
 wherein said blocking projection is respectively arranged at an end of a rocking lever which is moveable to a releasing position in which the drive mechanism is released by advancing an operating button, and can be reset into a locking position, in which the drive mechanism is locked, by a second restoring means.

12. A device for the controlled delivery of an injectable liquid from a liquid container sealed at a rear end by a piston which can be slid axially in said container to deliver the liquid from an outlet at a front end of the container, comprising:
 a substantially elongated flexible force transferring structure axially deviated behind the container away from a generally central longitudinal axis of the container;
 a drive mechanism coupled to said flexible force transferring structure; and
 a restoring means rotatably mounted inside said drive mechanism, wherein said restoring means applies a restoring force to said drive mechanism such that said drive mechanism axially advances the piston for delivering liquid from the container,
 wherein the substantially elongated flexible force transferring structure is guided by a guide which is configured to at least as far as possible inhibit the flexible force transferring structure from bending laterally, away from a plane in which said flexible force transferring structure lies.

13. The device as set forth in claim 12, wherein the guide is formed by a lower and an upper half-casing of the device and by at least one stay projecting substantially perpendicularly from a respective half-casing.

14. A device for the controlled delivery of an injectable liquid from a liquid container wherein:
 a flexible force transferring means comprising a cylindrical coil spring axially deviated behind the container away from a generally central longitudinal axis of the container transfers a drive force of a rotatable drive wheel to a piston which slides axially in the device;
 a restoring force of a spring is applied to the drive wheel to move the piston, said spring being rotatably mounted inside said drive wheel; and
 a locking means locks the drive wheel against rotation and releases the drive wheel for rotation.

15. The device of claim 14, wherein the amount of liquid delivered is indicated by audible clicks.

16. A device for the controlled delivery of an injectable liquid from a liquid container sealed at a rear end by a piston which can be slid axially in said container to deliver the liquid from an outlet at a front end of the container, comprising:

a flexible force transferring means axially deviated behind the container away from a generally central longitudinal axis of the container;

a drive mechanism coupled to said flexible force transferring means wherein said flexible force transferring means is mounted directly on an outer circumference of said drive mechanism; and a restoring means rotatably mounted inside said drive mechanism, wherein said restoring means applies a restoring force to said drive mechanism such that said drive mechanism axially advances the piston for delivering liquid from the container.

17. A device for the controlled delivery of an injectable liquid from a liquid container sealed at a rear end by a piston which can be slid axially in said container to deliver the liquid from an outlet at a front end of the container, comprising:

a drive wheel;

a flexible force transferring means axially deviated behind the container away from a generally central longitudinal axis of the container, wherein the flexible force transferring means is coupled to a lateral facing area of the drive wheel; and a restoring means rotatably mounted inside said drive mechanism, wherein said restoring means applies a restoring force to said drive mechanism such that said drive mechanism axially advances the piston for delivering liquid from the container.

18. The device as set forth in claim 17, wherein, absent a counter force, the restoring means permanently applies said restoring force to the drive mechanism in order to actuate it from a starting position in which the piston is situated substantially at the rear end of the liquid container to an end position in which the piston is situated substantially at the front end of the liquid container.

19. The device as set forth in claim 18, wherein, in the starting position of the piston, a region in which the flexible force transferring means is attached to the drive mechanism is substantially arranged diametrically opposite the rear end of the liquid container.

20. The device as set forth in claim 17, further comprising an adjustable locking means for providing controlled locking against an angular adjustment of the drive wheel.

21. The device as set forth in claim 20, wherein said locking means comprises a blocking projection which cooperates with an outer toothed area of the drive mechanism.

22. The device as set forth in claim 21, wherein said blocking projection is respectively arranged at an end of a rocking lever which is moveable to a releasing position in which the drive mechanism is released by advancing an operating button, and can be reset into a locking position, in which the drive mechanism is locked, by a second restoring means.

23. The device as set forth in claim 17, wherein the drive mechanism is configured, when delivering the liquid, to emit a number of clicks corresponding to the dosage of liquid delivered.

* * * * *